United States Patent
Lv et al.

(10) Patent No.: US 9,862,661 B2
(45) Date of Patent: Jan. 9, 2018

(54) PROCESS FOR THE PREPARATION OF 2, 3, 3, 3-TETRAFLUOROPROPENE

(71) Applicant: XI'AN MODERN CHEMISTRY RESEARCH INSTITUTE, Xi'an, Shaanxi (CN)

(72) Inventors: Jian Lv, Shaanxi (CN); Hui Ma, Shaanxi (CN); Jijun Zeng, Shaanxi (CN); Wei Zhang, Shaanxi (CN); Zhijun Hao, Shaanxi (CN); Sheng Han, Shaanxi (CN); Yongmei Du, Shaanxi (CN); Jianping Kang, Shaanxi (CN); Chunying Li, Shaanxi (CN); Fengxian Li, Shaanxi (CN)

(73) Assignee: Xi'an Modern Chemistry Research Institute, Xi'an (CN)

(*) Notice: Subject to any disclaimer, the term of this patent is extended or adjusted under 35 U.S.C. 154(b) by 0 days.

(21) Appl. No.: 15/535,300

(22) PCT Filed: Feb. 5, 2015

(86) PCT No.: PCT/CN2015/072305
§ 371 (c)(1),
(2) Date: Jun. 12, 2017

(87) PCT Pub. No.: WO2016/090745
PCT Pub. Date: Jun. 16, 2016

(65) Prior Publication Data
US 2017/0327441 A1    Nov. 16, 2017

(30) Foreign Application Priority Data

Dec. 13, 2014  (CN) .......................... 2014 1 0772306

(51) Int. Cl.
*C07C 17/23* (2006.01)
*C07C 17/25* (2006.01)
(Continued)

(52) U.S. Cl.
CPC ............. *C07C 17/23* (2013.01); *B01J 23/894* (2013.01); *B01J 23/8906* (2013.01);
(Continued)

(58) Field of Classification Search
CPC ....... C07C 17/25; C07C 21/18; C07C 17/383; C07C 17/206; C07C 19/08; C07C 17/093;
(Continued)

(56) References Cited

FOREIGN PATENT DOCUMENTS

CN        103508840     * 11/2014

* cited by examiner

*Primary Examiner* — Jafar Parsa
(74) *Attorney, Agent, or Firm* — Stites & Harbison, PLLC; David W. Nagle, Jr.; Terry L. Wright

(57) ABSTRACT

Disclosed is a process for the preparation of 2,3,3,3-tetrafluoropropene, comprising the following two reaction steps: a. a compound having the formula $CF_{3-x}Cl_xCF_{2-y}Cl_yCH_2Cl$ undergoes gas-phase fluorination with hydrogen fluoride through n serially-connected reaction vessels in the presence of a compound catalyst, producing 2,3-dichloro-1,1,1,2-tetrafluoropropane, 1,2,3-trichloro-1,1,2-trifluoropropane, and 1,3-dichloro-1,1,2,2-tetrafluoropropane; in said formula, x=1, 2, 3, y=1, 2, and 3≤x+y≤5; b. the 2,3-dichloro-1,1,1,2-tetrafluoropropane, 1,2,3-trichloro-1,1,2-trifluoropropane, and 1,3-dichloro-1,1,2,2-tetrafluoropropane undergo gas-phase dehalogenation with hydrogen in the presence of a dehalogenation catalyst, producing 2,3,3,3-tetrafluoropropene and 3-chloro-2,3,3-trifluoropropene, then separation and refining are performed, producing 2,3,3,3-tetrafluoropropene. The present invention is primarily used to produce 2,3,3,3-tetrafluoropropene.

12 Claims, 8 Drawing Sheets

(51) Int. Cl.
| | |
|---|---|
| *C07C 17/093* | (2006.01) |
| *C07C 21/18* | (2006.01) |
| *B01J 23/883* | (2006.01) |
| *C07C 17/383* | (2006.01) |
| *B01J 23/89* | (2006.01) |
| *B01J 27/138* | (2006.01) |
| *B01J 35/00* | (2006.01) |
| *C07C 17/20* | (2006.01) |
| *C07C 19/08* | (2006.01) |

(52) U.S. Cl.
CPC ......... *B01J 23/8986* (2013.01); *B01J 27/138* (2013.01); *B01J 35/0006* (2013.01); *C07C 17/206* (2013.01); *C07C 17/25* (2013.01); *C07C 17/383* (2013.01); *C07C 19/08* (2013.01); *C07C 21/18* (2013.01)

(58) Field of Classification Search
CPC .. B01J 35/0006; B01J 23/883; B01J 23/8906; B01J 23/894; B01J 23/8986
See application file for complete search history.

Figure 5

PROCESS FOR THE PREPARATION OF 2, 3, 3, 3-TETRAFLUOROPROPENE

TECHNICAL FIELD

The present invention relates to a process for the preparation of hydrofluoroolefins, and more particularly to a process for the preparation of 2,3,3,3-tetrafluoropropene (HFO-1234yf).

BACKGROUND ART

Hydrofluoroolefins (HFOs), as compared with chlorofluorocarbons (CFCs), Hydrochlorofluorocarbons (HCFCs), and hydrofluorocarbons (HFCs), do not contain chlorine and do not pose a threat to the Earth's ozone layer, meanwhile have a low Global Warming Potential, which have now become the focus of research in F-chemical industries. 2,3,3,3-tetrafluoropropene, i.e., HFO-1234yf, as one of hydrofluoroolefins, has an ozone depletion potential of 0, has a Global Warming Potential of 4, and can be widely used as refrigerants, extinguishing agents, heat-transfer media, propellants, foaming agents, blowing agents, gaseous media, sterilizing agent carriers, monomer of polymers, granular-removing fluids, carrier gas fluids, abrasive polishing agents, alternative desiccants and electrical cycle working fluids.

WO2009153493 discloses a process for the preparation of HFO-1234yf with 1,1,1,2,2,3-hexafluoropropane (HFC-236cb) as a raw material, in which HFC-236cb firstly undergoes dehydrofluorination in the presence of hydrogen and the catalyst Ni—Cr/AlF$_3$ to generate 1,2,3,3,3-pentafluoropropylene (HFC-1225ye), then HFC-1225ye undergoes hydrogenation to obtain 1,1,1,2,3-pentafluoropropane (HFC-245eb), and finally undergoes dehydrofluorination reaction in the presence of hydrogen to obtain HFO-1234yf.

US20110190554 discloses a process for the synthesis of HFO-1234yf with 1,1,2,3,3,3-hexafluoropropene (HFP) as a raw material by four steps of reactions including hydrogenation, dehydrofluorination, hydrogenation and dehydrofluorination.

In the above-mentioned two synthetic methods, the reaction materials are difficult to obtain, many reaction steps are required, the cost is high, and at least the stoichiometric amount of hydrogen is need to be introduced. The hydrogenation step usually uses a higher molar ratio in order to effectively control the exothermicity of the reaction. In addition, introduction of excessive hydrogen at a relatively high temperature will increase relevant safety risks, and the conditions are harsh, which are not conducive to industrial production.

US2011207975 discloses a process for the synthesis of HFO-1234yf with 1,1,2,3-tetrachloropropene (TCP) or 1,1,1,2,3-pentachloropropane (HCC-240db) as a raw material. In the method, firstly TCP or HCC-240db undergoes gas-phase fluorination with HF in the presence of Cr$_2$O$_3$ catalyst in a first reactor to obtain 2-chloro-3,3,3-trifluoropropene (HCFC-1233xf), and then HCFC-1233xf undergoes liquid-phase fluorination in a second reactor under the action of SbCl$_5$ to obtain 2-chloro-1,1,1,2-tetrafluoropropane (HCFC-244bb), and finally HCFC-244bb undergoes dehydrochlorination reaction in a third reactor to obtain HFO-1234yf.

WO2012099776 discloses a process for the preparation of HFO-1234yf from TCP by integrated three steps via HCFC-1233xf and HCFC-244bb.

WO2009125199 discloses a process for the preparation of HFO-1234yf from 2,3-dichloro-1,1,1-trifluoropropane (HCFC-243db) via HCFC-1233xf and HCFC-244bb.

For the above-mentioned preparation methods, firstly, they relate to chromium-based catalysts such as Cr$_2$O$_3$ and Cr$_2$O$_3$ supported on alumina or fluorinated alumina. In fact, the catalysts used in industrial production and application of HFCs are also chromium-based catalysts. These chromium-containing compounds and catalysts will cause damage to human digestive tract and kidney, especially high-valence chromium has a strong carcinogenic effect, and they are unfriendly to human and the environment in the process of production and use, and will cause serious harm. Secondly, the above methods all relate to the intermediates HCFC-1233xf and HCFC-244bb. These two halogenated hydrocarbons have approximate boiling points and azeotrope-like properties, and both of them are also easy to form an azeotrope with HF. Hence, a problem of difficult separation occurs, and the mixtures of them cannot be separated effectively by standard process and conventional methods, especially when they form a binary azeotrope or azeotrope-like component. Additionally, it has been found that during the preparation of HFO-1234yf from HCFC-244bb by dehydrochlorination, the HCFO-1233xf and HF impurities contained therein can seriously affect the life and product selectivity of the dehydrochlorination catalyst, and easily lead to a decrease in HFO-1234yf selectivity and in activity of the catalyst and loss of the catalyst life.

Although many methods have been currently disclosed for preparing HFO-1234yf, they have the deficiencies such as the harsh reaction conditions, unfriendliness of the catalyst to environment, difficulty in separating the reaction intermediates, energy consumption and cost increase due to too many reaction steps, and low selectivity of the target product. Thus, there is a need for continuous improvement and more effective preparation methods.

SUMMARY OF THE INVENTION

The purpose of the present invention is to overcome the shortcomings in the background art and to provide a process for the preparation of 2,3,3,3-tetrafluoropropene (HFO-1234yf), in which the reaction step is less, the intermediates are easy to separate, the catalysts are environmentally friendly, and the reaction conditions are mild.

To achieve the purpose of the present invention, the present invention provides a process for the preparation of 2,3,3,3-tetrafluoropropene, comprising the following steps:

(a) a compound having the formula $CF_{3-x}Cl_xCF_{2-y}Cl_yCH_2Cl$ undergoes gas-phase fluorination with hydrogen fluoride in the presence of a compound catalyst through n serially-connected reactors to produce a product stream comprising 2,3-dichloro-1,1,1,2-tetrafluoropropane, 1,2,3-trichloro-1,1,2-trifluoropropane, 1,3-dichloro-1,1,2,2-tetrafluoropropane, hydrogen chloride and unreacted hydrogen fluoride; wherein in the compound formula, x=1, 2 or 3, y=1 or 2, and $3 \leq x+y \leq 5$;

(b) 2,3-dichloro-1,1,1,2-tetrafluoropropane, 1,2,3-trichloro-1,1,2-trifluoropropane, and 1,3-dichloro-1,1,2,2-tetrafluoropropane undergo gas-phase dehalogenation with hydrogen in the presence of a dehalogenation catalyst to produce a product stream comprising 2,3,3,3-tetrafluoropropene, 3-chloro-2,3,3-trifluoropropene, hydrogen chloride and unreacted hydrogen;

(c) the product stream of step (a) enters into the first rectification column for hydrogen chloride separation, and the component from the top of the column which is hydrogen chloride, enters into an acid production system to obtain hydrochloric acid; the components from the bottom of the column which are 2,3-dichloro-1,1,1,2-tetrafluoropropane, 1,2,3-trichloro-1,1,2-trifluoropropane, 1,3-dichloro-1,1,2,2-tetrafluoropropane and hydrogen fluoride, enter into an phase separator for phase separation; the phase separation temperature is −30° C. to 0° C., the phase separator bottom materials 2,3-dichloro-1,1,1,2-tetrafluoropropane, 1,2,3-trichloro-1,1,2-trifluoropropane and 1,3-dichloro-1,1,2,2-tetrafluoropropane are subjected to acid-removal and drying, and then are transported as raw materials of step (b) to a dehalogenation reactor for dehalogenation reaction; and (d) the product stream of step (b) enters into the second rectification column, the component from the bottom of the column which is 3-chloro-2,3,3-trifluoropropene, is subjected to acid-removal and drying, and then is recycled to the serially-connected reactors of step (a); the components from the top of the column which are 2,3,3,3-tetrafluoropropene, hydrogen chloride and hydrogen, enter into the third rectification column; in the third rectification column, the components from the top of the column which are hydrogen and hydrogen chloride, enter into the hydrogen recovery system, the hydrogen is recycled to a dehalogenation reactor for dehalogenation reaction, and the components from the bottom of the column which are 2,3,3,3-tetrafluoropropene and hydrogen chloride, are subjected to refining and drying to produce the target product 2,3,3,3-tetrafluoropropene.

Other technical features of the present invention are as follows:

The compound having the formula $CF_{3-x}Cl_xCF_{2-y}Cl_yCH_2Cl$ in step (a) is $CCl_3CCl_2CH_2Cl$, $CFCl_2CCl_2CH_2Cl$ or $CF_2ClCCl_2CH_2Cl$.

The compound having the formula $CF_{3-x}Cl_xCF_{2-y}Cl_yCH_2Cl$ in step (a) is $CCl_3CCl_2CH_2Cl$.

The compound catalyst in step (a) is a Mn-A-B-C compound catalyst, wherein A is a Group VIII element, B is a high-field-strength element, and C is an alkaline-earth metal element; the molar ratio of Mn, A, B and C is (0.3-2):(0.6-5):(0.1-1):(2-9); the process for the preparation of catalyst comprises the following steps: a mixed solution of soluble salts of the three metals Mn, A and B is reacted with the precipitant in proportion, the pH is controlled at 7.5 to 9.5, stirring, precipitating, filtering and drying are conducted, then an oxide, hydroxide or carbonate of C is well mixed therewith, then staged calcination is performed at 200° C. to 500° C. under a condition of no less than three temperature gradients, and finally activation treatment is carried out with hydrogen fluoride at 200° C. to 380° C. to obtain the catalyst.

In the Mn-A-B-C compound catalyst in step (a), A is one of Ni, Fe and Co or a combination of two or more thereof, B is one of Zr, Y and La or a combination of two or more thereof, and C is one of Mg, Ca and Ba; and the molar ratio of Mn, A, B and C is (0.6-1):(2-4):(0.4-1):(4-7).

The Mn-A-B-C compound catalyst in step (a) is Mn—Ni—Zr—Ca compound catalyst, wherein the molar ratio of Mn, Ni, Zr and Ca is 0.6:3:0.4:6.

The n serially-connected reactors in step (a) are three serially-connected reactors arranged in series in the flowing direction of the raw material and charged with the same catalyst, which have sequentially increased reaction temperatures.

The increasing range of the reaction temperature between the three serially-connected reactors is 60° C. to 80° C.

At least a separation tank is installed between the primary and secondary reactors in the three serially-connected reactors, the components from the top of the separation tank which are 2,3,3,3-tetrafluoropropene and hydrogen chloride, enter into a second rectification column; the components from the bottom of the separation tank are 1,1,2,2,3-pentachloro-1-fluoropropane and/or 1,2,2,3-tetrachloro-1,1-difluoropropane or 1,1,1,2,2,3-hexachloropropane and hydrogen fluoride.

The conditions for the gas-phase fluorination reaction in the primary reactor of the three serially-connected reactors in step (a) are as follows: the reaction temperature is 150° C. to 180° C., the molar ratio of hydrogen fluoride to $CCl_3CCl_2CH_2Cl$ is (3-20):1, and the reaction contact time is 0.5 to 30 seconds.

The dehalogenation catalyst in step (b) is Cu—V—Mg—F catalyst in which the molar ratio of Cu, V and Mg is (2-4):(1-2):(4-7).

The conditions for the gas-phase dehalogenation in step (b) are as follows: the reaction temperature is 200° C. to 300° C., the molar ratio of hydrogen to the total amount of 2,3-dichloro-1,1,1,2-tetrafluoropropane, 1,2,3-trichloro-1,1,2-trifluoropropane and 1,3-dichloro-1,1,2,2-tetrafluoropropane is (0-1):1, and the contact time is 1 to 30 seconds.

The component from the bottom of the column 3-chloro-2,3,3-trifluoropropene of the second rectification column from step (d) is recycled to the primary reactor of the serially-connected reactors described in step (a).

The present invention, as compared with the prior art, has the following advantages: it provides a process for efficiently preparing HFO-1234yf with less reaction steps (only two steps are needed), while the processes disclosed in the reference documents often require three steps or even four steps; the intermediates are easy to separate, specifically, the differences between the boiling points of the intermediates 2,3-dichloro-1,1,1,2-tetrafluoropropane (bp: 53° C. to 55° C.), 1,2,3-trichloro-1,1,2-trifluoropropane (bp: 95° C. to 97° C.), 1,3-dichloro-1,1,2,2-tetrafluoropropane (bp: 69° C. to 71° C.), and 3-chloro-2,3,3-trifluoropropane (bp: 11° C. to 13° C.) are great, so the intermediates are easy to separate; in addition, the boiling points of the intermediates are greatly different from the target product HFO-1234yf (bp: −28° C.), wherein the difference between the boiling point of 3-chloro-2,3,3-trifluoropropene and that of the target product reaches 41° C., and the difference between the boiling point of 2,3-dichloro-1,1,1,2-tetrafluoropropane and that of the target product reaches 71° C.; the reaction catalysts do not involve chromium-containing compounds, and they are friendly to humans and environment; and the process has mild reaction conditions, the gas-phase reaction temperature does not exceed 340° C., and the most important is that the dehalogenation reaction is achieved in the presence of a small amount of hydrogen and does not need the stoichiometric amount of hydrogen.

DESCRIPTION OF DRAWINGS

FIGS. 2 to 5 are GC-MS spectrum, $^1$H-NMR spectrum, $^{13}$C-NMR spectrum, and $^{19}$F-NMR spectrum of the product HCFC-234bb;

DETAILED DESCRIPTION OF THE PRESENT APPLICATION

Figure 1:
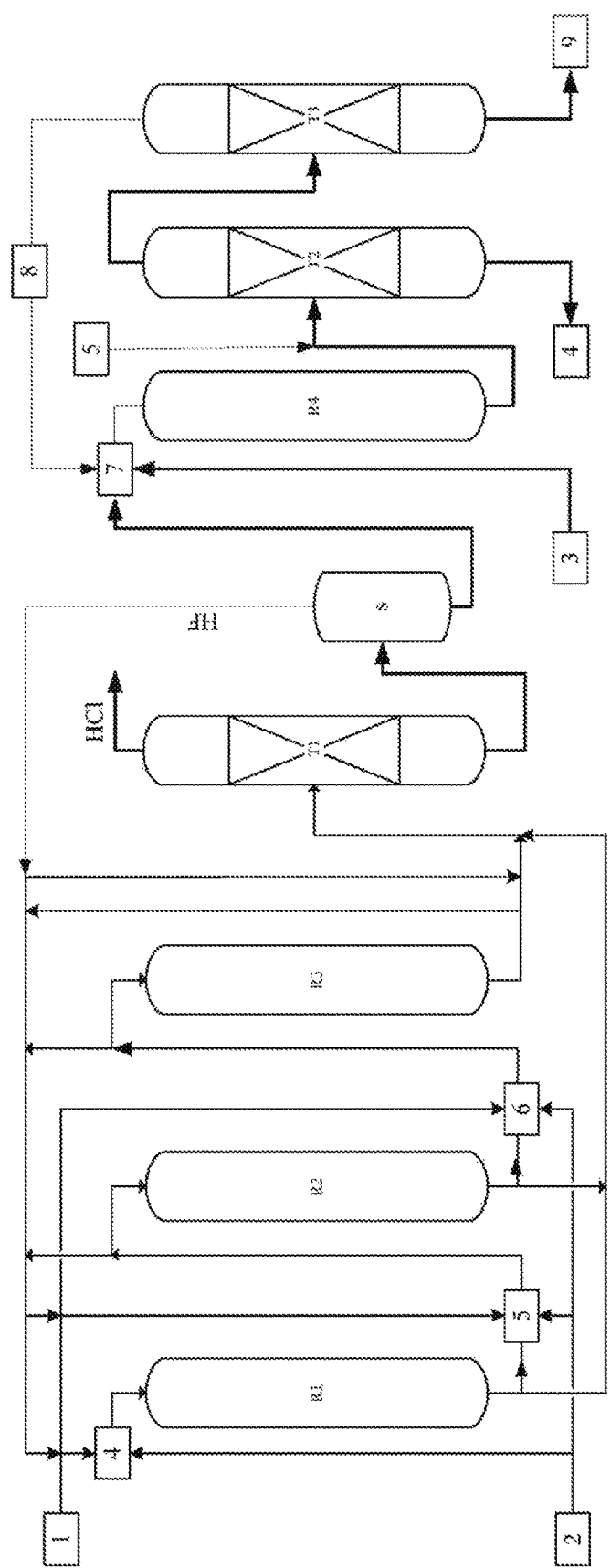
FIG. 1 is a schematic flow of the preparation of 2,3,3,3-tetrafluoropropene, wherein R1 is a primary reactor, R2 is a secondary reactor, R3 is a tertiary reactor, R4 is a dehalogenation reactor, T1 is a first rectification column, T2 is a second rectification column, T3 is a third rectification column, S is a phase separator, 1 is reaction materials, 2 is hydrogen fluoride, 3 is hydrogen, 4, 6 and 7 are static mixers, 5 is a separation tank (or a separation tank and a static mixer), 8 is a hydrogen recovery system, and 9 is a HFO-1234yf refining system.

In the present invention, 2,3,3,3-tetrafluoropropene (HFO-1234yf) is generated with a compound having the formula $CF_{3-x}Cl_xCF_{2-y}Cl_yCH_2Cl$ as a starting material by two-steps of reaction, gas-phase fluorination and gas-phase dechlorination. The reaction process is as follows:

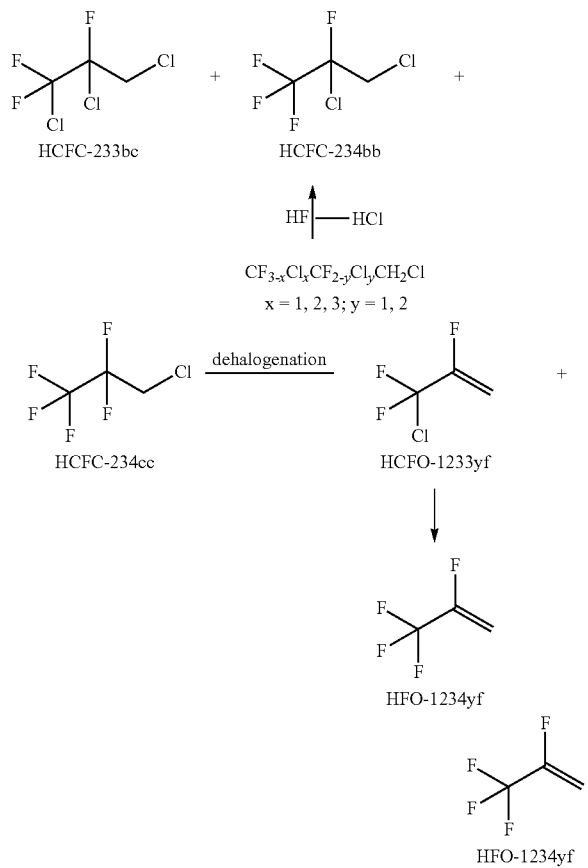

The process for the preparation of HFO-1234yf of the present invention comprises the following steps:

(a) a compound having the formula $CF_{3-x}Cl_xCF_{2-y}Cl_yCH_2Cl$ undergoes gas-phase fluorination with hydrogen fluoride in the presence of a compound catalyst through n serially-connected reactors to produce a product stream comprising 2,3-dichloro-1,1,1,2-tetrafluoropropane (HCFC-234bb), 1,2,3-trichloro-1,1,2-trifluoropropane (HCFC-233bc), 1,3-dichloro-1,1,2,2-tetrafluoropropane (HCFC-234cc), HCl and unreacted HF; wherein in the compound formula, x=1, 2 or 3, y=1 or 2, and $3 \le x+y \le 5$;

(b) HCFC-234bb, HCFC-233bc, and HCFC-234cc undergo gas-phase dehalogenation with $H_2$ in the presence of a dehalogenation catalyst to produce a product stream comprising HFO-1234yf, 3-chloro-2,3,3-trifluoropropene (HCFO-1233yf), HCl and unreacted $H_2$;

(c) the product stream of step (a) enters into a first rectification column for hydrogen chloride separation, and the component from the top of the column which is HCl, enters into an acid production system to obtain hydrochloric acid; the components from the bottom of the column which are HCFC-234bb, HCFC-233bc, HCFC-234cc and HF, enter into an phase separator for phase separation; the phase separation temperature is −30° C. to 0° C., the phase separator bottom materials HCFC-234bb, HCFC-233bc and HCFC-234cc are subjected to acid-removal and drying, and then are transported as raw materials of step (b) to a dehalogenation reactor for dehalogenation reaction;

(d) the product stream of step (b) enters into the second rectification column, the component from the bottom of the column which is HCFO-1233yf, is subjected to acid-removal and drying, and then is recycled to the serially-connected reactors of step (a); the components from the top of the column which are HFO-1234yf, HCl and $H_2$, enter into a third rectification column; in the third rectification column, the components from the top of the column which are $H_2$ and HCl, enter into the hydrogen recovery system, and then are recycled to a dehalogenation reactor for dehalogenation reaction, and the components from the bottom of the column which are HFO-1234yf and HCl, are subjected to refining and drying to produce the target product HFO-1234yf.

The compound having the formula $CF_{3-x}Cl_xCF_{2-y}Cl_yCH_2Cl$ in step (a) of the present invention is $CCl_3CCl_2CH_2Cl$, $CFCl_2CCl_2CH_2Cl$ or $CF_2ClCCl_2CH_2Cl$, and of course suitable compounds also include $CCl_3CFClCH_2Cl$ and $CFCl_2CFClCH_2Cl$. The starting material can be selected in a wide range, but in comprehensive consideration, $CCl_3CCl_2CH_2Cl$ and $CCl_3CFClCH_2Cl$ are preferred, and $CCl_3CCl_2CH_2Cl$ is more preferred. Of course suitable starting material can also be $CF_2ClCFClCH_2Cl$ or $CF_3CCl_2CH_2Cl$, with the only difference that the products generated under the reaction conditions of step (a) are mainly HCFC-234bb, HCFC-234cc and 3-chloro-1,1,1,2,2-pentafluoropropane (HCFC-235cb); and the starting material can also be $CCl_3CF_2CH_2Cl$, $CFCl_2CF_2CH_2Cl$ or $CF_2ClCF_2CH_2Cl$, with the only difference that the products generated under the reaction conditions of step (a) are mainly HCFC-234cc and HCFC-235cb.

The n serially-connected reactors in step (a) are n serially-connected reactors arranged in series in the flowing direction of the raw material and charged with the same catalyst, which have sequentially increased reaction temperatures; a static mixer, a heat exchanger, a phase separator, a separation tank, a rectification column or other simple separation devices can be installed between the serially-connected reactors according to requirements to promote the removal and separation of hydrogen chloride or to improve the reaction effect; at least a separation tank is installed between the primary and secondary reactors of the three serially-connected reactors; the gas inlet of the static mixer (separation tank) is connected with a hydrogen fluoride replenishment pipeline, the liquid inlet is connected with the liquid material outlet pipeline of the adjacent previous reactor, and the outlet is connected with the inlet of the adjacent posterior reactor; and the products of each reactor can selectively enter into the subsequent separation section and/or into at least one of the remaining reactors, wherein n is no less than 2, preferably n=3; when the catalyst in one of the reactors of the serially-connected reactor is inactivated, the reactor can be isolated from the apparatus to perform regeneration of the catalyst. The conversion rate and product distribution of each reactor are mainly controlled by the reaction temperature, the retention time and the ratio of materials. In the embodiment, the reaction temperature in the primary reactor R1 is 150° C. to 180° C., and an appropriate increasing range of the reaction temperature is 60° C. to 80° C. In a preferred embodiment, the reaction conditions of R1 are as follows: the reaction temperature is 150° C. to 180° C., the molar ratio of hydrogen fluoride to $CCl_3CCl_2CH_2Cl$ is (3-20):1, and the reaction contact time is 0.5 to 30 seconds, the reaction of the starting material $CCl_3CCl_2CH_2Cl$ occurs under the action of the compound catalyst in primary reactor R1, the product stream thereof mainly comprises the resulting $CFCl_2CCl_2CH_2Cl$, $CF_2ClCCl_2CH_2Cl$, HCl, and unreacted $CCl_3CCl_2CH_2Cl$ and HF; the reaction conditions of the secondary reactor R2 are as follows: the reaction temperature is 210° C. to 260° C., the molar ratio of hydrogen fluoride to the organic matters in the product from the primary reactor is (10-15):1, the reaction contact time is 5 to 20 seconds, and the product stream thereof mainly comprises $CF_2ClCCl_2CH_2Cl$, $CF_2ClCFClCH_2Cl$, $CF_3CFClCH_2Cl$, HCl and HF; and the reaction conditions of the tertiary reactor R3 are as follows: the reaction temperature is 270° C. to 340° C., the molar ratio of hydrogen fluoride to the organic matters in the product from the secondary reactor is (5-20):1, the reaction contact time is 10 to 30 seconds, and the product stream thereof comprises $CF_3CFClCH_2Cl$, $CF_2ClCFClCH_2Cl$, $CF_2ClCF_2CH_2Cl$, $CF_3CF_2CH_2Cl$, HCl, and HF.

The main intermediates $CFCl_2CCl_2CH_2Cl$ (HCFC-231ab), $CF_2ClCCl_2CH_2Cl$ (HCFC-232ac), $CF_2ClCFClCH_2Cl$ (HCFC-233bc), $CF_3CFClCH_2Cl$ (HCFC-234bb), $CF_2ClCF_2CH_2Cl$ (HCFC-234cc) and $CF_3CF_2CH_2Cl$ (HCFC-235cb) involved in the primary, secondary and tertiary reactors in step (a) of the present invention have a boiling point of 178° C. to 180° C., 141° C. to 143° C., 95° C. to 97° C., 53° C. to 55° C., 69° C. to 71° C., and 28° C. to 30° C., respectively, the difference of which is great. Hence, the intermediates are easy to separate, and effective separation thereof can be achieved by conventional separation means.

The compound catalyst in step (a) of the present invention is Mn-A-B-C compound catalyst, wherein A is a group VIII element; B is a high-field-strength element, i.e., an element having a relatively high ionic valence, a relatively small radius, and a relatively high ion field strength, including lanthanide such as Sc and Y, Th, U, Pb, Zr, Hf, Ti, Nb and Ta; and C is an alkaline-earth metal element. A is preferably one of Ni, Fe and Co or a combination of two or more thereof, B is preferably one of Zr, Y and La or a combination of two or more thereof, and C is preferably one of Mg, Ca and Ba; and the molar ratio of Mn, A, B and C is (0.3-2):(0.6-5):(0.1-1):(2-9), preferably (0.6-1):(2-4):(0.4-1):(4-7), and more preferably 0.6:3:0.4:6.

The weight percentage contents of 2,3-dichloro-1,1,1,2-tetrafluoropropane, 1,2,3-trichloro-1,1,2-trifluoropropane, 1,3-dichloro-1,1,2,2-tetrafluoropropane and 3-chloro-1,1,1,2,2-pentafluoropropane in the products of step (a) of the present invention can be adjusted by means of catalyst, reaction temperature, molar ratio and contact time according to requirements. The contents of 2,3-dichloro-1,1,1,2-tetrafluoropropane and 1,2,3-trichloro-1,1,2-trifluoropropane can be adjusted in a wide range, 2,3-dichloro-1,1,1,2-tetrafluoropropane can be adjusted in a range of 10% to 95%, and 1,2,3-trichloro-1,1,2-trifluoropropane can be adjusted in a range of 5% to 60%.

The reaction in step (a) of the present invention may be carried out in any reactor suitable for the gas-phase fluorination reaction. The type of the fluorination reactor in step (a) is not critical, and tubular reactors, fluidized-bed reactors and the like can be used. In addition, an adiabatic reactor or isothermal reactor may also be used.

The dehalogenation reaction in step (b) of the present invention is a gas-phase dehalogenation reaction in the presence of a dehalogenation catalyst, and the dehalogenation catalyst is a Cu—V—Mg—F catalyst. The process for the preparation of the catalyst comprises the following steps: $V_2O_5$ is added to a mixed aqueous solution of $Cu(NO_3)_2 \cdot 3H_2O$ and $Mg(NO_3)_2 \cdot 6H_2O$ according to a certain proportion, 10% (by mass) ammonium bicarbonate is added, the pH is adjusted to about 9, and the reaction is carried out for about 5 h. The product is washed, centrifugally separated, dried at 120° C., calcined by stages at 200° C. to 500° C. under a condition of no less than three temperature gradients, and finally activated with hydrogen fluoride and hydrogen in order to obtain the catalyst, wherein the molar ratio of Cu, V and Mg is (2-4):(1-2):(4-7), preferably (3-4):(1-2):(4-6), more preferably 4:1:5. Suitable processes for the preparation of the catalyst further include impregnation method, coprecipitation method, blending method and sol-gel method and the like. Of course, the dehalogenation reaction may also be a liquid phase dehalogenation reaction in which HCFC-234bb, HCFC-233bc and HCFC-235cb react with a reducing agent in a protonic solvent, wherein the protonic solvent includes methanol, ethanol, acetic acid or ethylene glycol, and of course it may also be tert-butanol, formic acid, acetic anhydride, glycerol or diethylene glycol, meanwhile other common protonic solvents, such as propylene glycol, polyethylene glycol 200 and polyhydric alcohol in which the hydroxyl groups are not fully protected, are also suitable for the step; the reducing agent is Mg, Al, Zn or Fe, or a bimetallic reducing system of Ag and Fe, and it may also be a composition of Cu, Ag, Ni and Fe, a composition of Cu and Fe, a composition of Cu and Al, a composition of Pd and Fe, and combinations thereof.

The gas-phase dehalogenation reaction in step (b) of the present invention can achieve conversion to 1234yf at a relatively low reaction temperature of 200° C. to 300° C. with a relatively high conversion rate and high selectivity. The molar ratio of hydrogen to the total amount of HCFC-234bb, HCFC-233bc and HCFC-234cc in the gas-phase dehalogenation reaction is a key factor that affecting the reaction. When excessive hydrogen is introduced, the selectivity of the target product is significantly reduced although complete conversion can be achieved. A suitable molar ratio of hydrogen to the total amount of HCFC-234bb, HCFC-233bc and HCFC-234cc is (0-1):1, preferably (0.1-0.5):1, more preferably (0.1-0.3):1. Hydrogen may be introduced intermittently, semi-continuously or continuously. And the contact time for the gas-phase dehalogenation reaction is selected in the range of 1 to 60 seconds according to the amount of the introduced hydrogen, preferably 5 to 30 seconds.

The boiling points of the products HFO-1234yf and HCFO-1233yf generated in step (b) of the present invention are about −28° C. and 11° C. to 13° C., respectively, and the boiling points are greatly different from the boiling points of the reaction materials for dehalogenation, i.e. HCFC-233bc and HCFC-234cc. Therefore, the products are easy to separate.

The product HCFO-1233yf of step (d) of the present invention is recycled to the primary reactor of the serially-connected reactors in step (a), and at this time the product stream of the primary reactor R1 comprises the generated HFO-1234yf, $CFCl_2CCl_2CH_2Cl$, $CF_2ClCCl_2CH_2Cl$, HCl and unreacted $CCl_3CCl_2CH_2Cl$ and HF; the above-mentioned product stream enters into the separation tank between the primary reactor and the secondary reactor in the serially-connected reactors, the components from the top of the separation tank which are 2,3,3,3-tetrafluoropropene and hydrogen chloride, enter into the second rectification column; the components from the bottom of the separation tank which are 1,1,2,2,3-pentachloro-1-fluoropropane and/or 1,2, 2,3-tetrachloro-1,1-difluoropropane or 1,1,1,2,2,3-hexachloropropane and hydrogen fluoride, enter into the secondary reactor R2 via a static mixer and/or heat exchanger.

In the embodiment of steps (a) and (b) of the present invention, preferably the process stream is passed down through the catalyst bed layer. The catalyst is preferably dried, preheated and activated prior to each use. It may also be advantageous to periodically regenerate the catalyst in situ in the reactor after use for a long time. The pretreatments of the fluorination catalyst and dechlorination catalyst in steps (a) and (b) can be carried out by heating the catalyst to about 200° C. to about 380° C. in nitrogen or other inert gas stream, and then treating and activating the catalyst with a hydrogen fluoride stream that is diluted with highly excessive nitrogen to obtain high catalyst activity. The dechlorination catalyst used in step (c) further needs to be activated in a hydrogen atmosphere. The regeneration of the catalysts can be carried out under the following conditions: air or air diluted with nitrogen is allowed to pass through the catalyst at a temperature of about 100° C. to about 380° C., preferably about 150° C. to about 365° C., for about 8 hours to about 3 days depending on the size of the reactor.

The present invention will now be described in further detail with reference to the examples.

Analytical Instruments: Haixin Gas Chromatograph GC-930, Agilent 30 m DB-5 (50 m×0.32 mm) capillary chromatographic column; ITQ 700 (ion trap): Thermofisher scientific, Agilent GASPRO (60 m×0.25 mm) capillary chromatographic column.

Chromatographic conditions: an initial column temperature of 40° C., keeping for 5 min, heating at a rate of 10° C./min to 180° C., and keeping for 3 min; a vaporizing chamber temperature of 220° C., and a split ratio of 50.

The conditions for ion trap mass spectrometry: a filament emission current of 70 A; a mass scanning range of 10-350 amu; full scan mode, a scan speed of 10 micro-scan/sec; a multiplier voltage of 1556V; a transmission line temperature of 220° C., and helium as carrier gas.

The schematic flow for the preparation of 2,3,3,3-tetrafluoropropene is further explained below.

The reaction material 1 was first fully mixed with hydrogen fluoride 2 in the static mixer 4, then introduced into the primary reactor R1, secondary reactor R2 and tertiary reactor R3 successively to carry out reaction. The resulting mixture at the bottom of the primary reactor R1 passed through the separation tank 5, then well mixed with hydrogen fluoride 5 in the static mixer 5 (if necessary, a heat exchanger is installed between R1 and the static mixer 5), and then introduced into the secondary reactor R2 to carry out reaction. The resulting mixture at the bottom of the secondary reactor R2 was well mixed with hydrogen fluoride in the static mixer 6, and then introduced into the tertiary reactor R3 to carry out reaction. The reaction product entered into the first rectification column T1 for HCl separation, the component from the top of the column which was hydrogen chloride, entered into the acid production system to obtain hydrochloric acid, and the components from the bottom of the column which were 2,3-dichloro-1,1,1,2-tetrafluoropropane, 1,2,3-trichloro-1,1,2-trifluoropropane, 1,3-dichloro-1,1,2,2-tetrafluoropropane, 3-chloro-1,1,1,2,2-pentafluoropropane and hydrogen fluoride, entered into an phase separator S for phase separation; the phase separation temperature was −30° C. to 0° C., the phase separator bottom materials, i.e. 2,3-dichloro-1,1,1,2-tetrafluoropropane, 1,2,3-trichloro-1,1,2-trifluoropropane, 1,3-dichloro-1,1,2,2-tetrafluoropropane and 3-chloro-1,1,1,2,2-pentafluoropropane were subjected to acid-removal and drying, and then transported to the dehalogenation reactor R4.

According to the product distribution in each reactor, the reaction temperatures in the reactors were adjusted, the ratio of the materials was adjusted or compensated, or even the flow direction of the material was changed to achieve continuous serial operation and generate the product which then introduced into the product separation stage.

When the catalyst in reactor R1 was inactivated, the reactor R1 was isolated from the system for regeneration of the catalyst. The reaction material 1 was well mixed with hydrogen fluoride 2 in the static mixer 4, and then introduced into the reactors R2 and R3 successively to carry out reaction. After regeneration of the catalyst in the reactor R1 was finished, the order for the raw materials to enter was R2, R3 and R1. The products were discharged from the bottom of the reactor R1.

Hydrogen 3 was well mixed with the phase separator bottom materials 2,3-dichloro-1,1,1,2-tetrafluoropropane, 1,2,3-trichloro-1,1,2-trifluoropropane, 1,3-dichloro-1,1,2,2-tetrafluoropropane, and 3-chloro-1,1,1,2,2-pentafluoropropane in the static mixer 7, and then entering into the dehalogenation reactor R4 to carry out reaction. The reaction products entered into the second rectification column T2 to carry out separation, the components from the top of the column which were 2,3,3,3-tetrafluoropropene, hydrogen chloride and hydrogen, entered into the third rectification column T3 to carry out separation, and the component from the bottom of the column which was 3-chloro-2,3,3-trifluoropropene, was subjected to acid-removal and drying, and recycled to the primary reactor R1. The reaction products of R1 entered into the separation tank 4, and the components from the top of the separation tank which were HFO-1234yf and the hydrogen chloride, entered into the second rectification column T2. In the third rectification column T3, the components from the top of the column which were hydrogen and hydrogen chloride, were introduced into the hydrogen recovery system 8, and then recycled to the dehalogenation reactor R4, and the components from the bottom of the column which were 2,3,3,3-tetrafluoropropene and hydrogen chloride, were introduced into the target product refining system 9, and subjected to refining and drying processes to obtain the target product HFO-1234yf.

Examples 1

Preparation of catalyst: manganese acetate, nickel nitrate, zirconium chloride were mixed according to a certain proportion to form 2 mol/L aqueous solution, and then 15% (by mass) ammonia water was added dropwise at 20° C. to 40° C. under continuous stirring, the pH was adjusted to about 8.0, and reaction was carried out for 8 h. The reaction product was filtered, dried at 120° C. for 2 h, uniformly mixed with a certain amount of calcium carbonate, and calcined as follows: calcining at 200° C. for 1 h, heating at a rate of 5° C./min to 320° C., calcining for 2 h, heating at a rate of 10° C./min to 450° C. and calcining for 4 h. Finally, the product was activated with hydrogen fluoride at 200° C. to 380° C. for about 36 h to obtain catalyst.

To a fixed-bed tubular reactor made of nickel tube and having an inner diameter of 38 mm, 50 ml of the Mn—Ni—Zr—Ca compound catalyst in which the molar ratio of Mn, Ni, Zr and Ca is 0.6:3:0.4:6 was charged, and the catalyst was dried. Afterward, HF and $CCl_3CCl_2CH_2Cl$ (HCC-230ab) were introduced into the primary reactor R1 at 160° C., and the product stream thereof which mainly contains $CFCl_2CCl_2CH_2Cl$ (HCFC-231ab, abbreviated as 231ab) flowed through the separation tank and static mixer into the secondary reactor (R2). The product stream from the secondary reactor which mainly contains $CF_2ClCFClCH_2Cl$ (HCFC-233bc, abbreviated as 233bc) and $CF_2ClCCl_2CH_2Cl$ (HCFC-232ac, abbreviated as 232ac) entered into the tertiary reactor (R3) for reaction. The temperature of the secondary reactor was 230° C., and the temperature of the tertiary reactor was 310° C. For the three reactions, all of them were carried out under atmospheric pressure (normal pressure), the molar ratio of HF to organic matters was controlled at 10:1, 15:1 and 10:1, respectively, and the contact time was 5 s, 15 s and 20 s, respectively. The reaction products were washed with water and alkali to remove HCl and HF, and analyzed by gas chromatography and mass spectrometry. The reaction results were as follows: a small amount of by-products such as $CF_3CF_2CH_2Cl$ (HCFC-235cb), $CF_3CCl=CClH$ (HCFO-1223xd) and $CF_3CF=CClH$ (HCFO-1224yd) appeared while $CF_3CFClCH_2Cl$ (HCFC-234bb), HCFC-233bc and $CF_2ClCF_2CH_2Cl$ (HCFC-234cc) were generated, and the main results were shown in Table 1.

The above-mentioned liquid reaction products were rectified at atmospheric pressure, and the product having a boiling range of 53° C. to 55° C. was collected with a purity of 99.2%. After characterized by GC-MS, $^1$H-NMR, $^{13}$C-NMR and $^{19}$F-NMR, the product was identified as HCFC-234bb, as shown in FIGS. 2 to 5.

Figure 2:
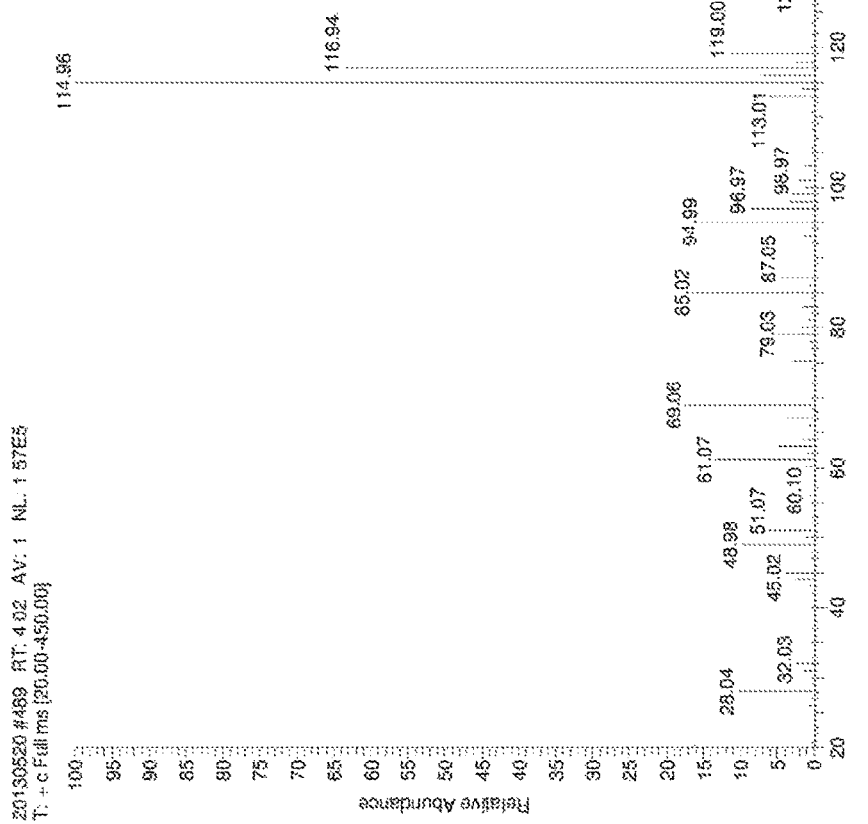

The mass spectrum results as shown in FIG. 2 and assignment of the peaks therein were as follows: m/z184: m/z186:m/z188=9:6:1 (M+), which is an isotope peak ratio for the fragment containing two chlorine atoms; m/z149:m/z151=3:1 [(M-Cl)+], which is an isotope peak ratio for the fragment containing one chlorine atom; m/z165:m/z167:m/z169=9:6:1[(M-F)+], the loss is reasonable; m/z69 (CF3+) and m/z115 (C2H2FCl2+) were complementary ions; m/z75 (C3HF2+); and m/z49:m/z51=3:1 (CH2Cl+).

Figure 3:
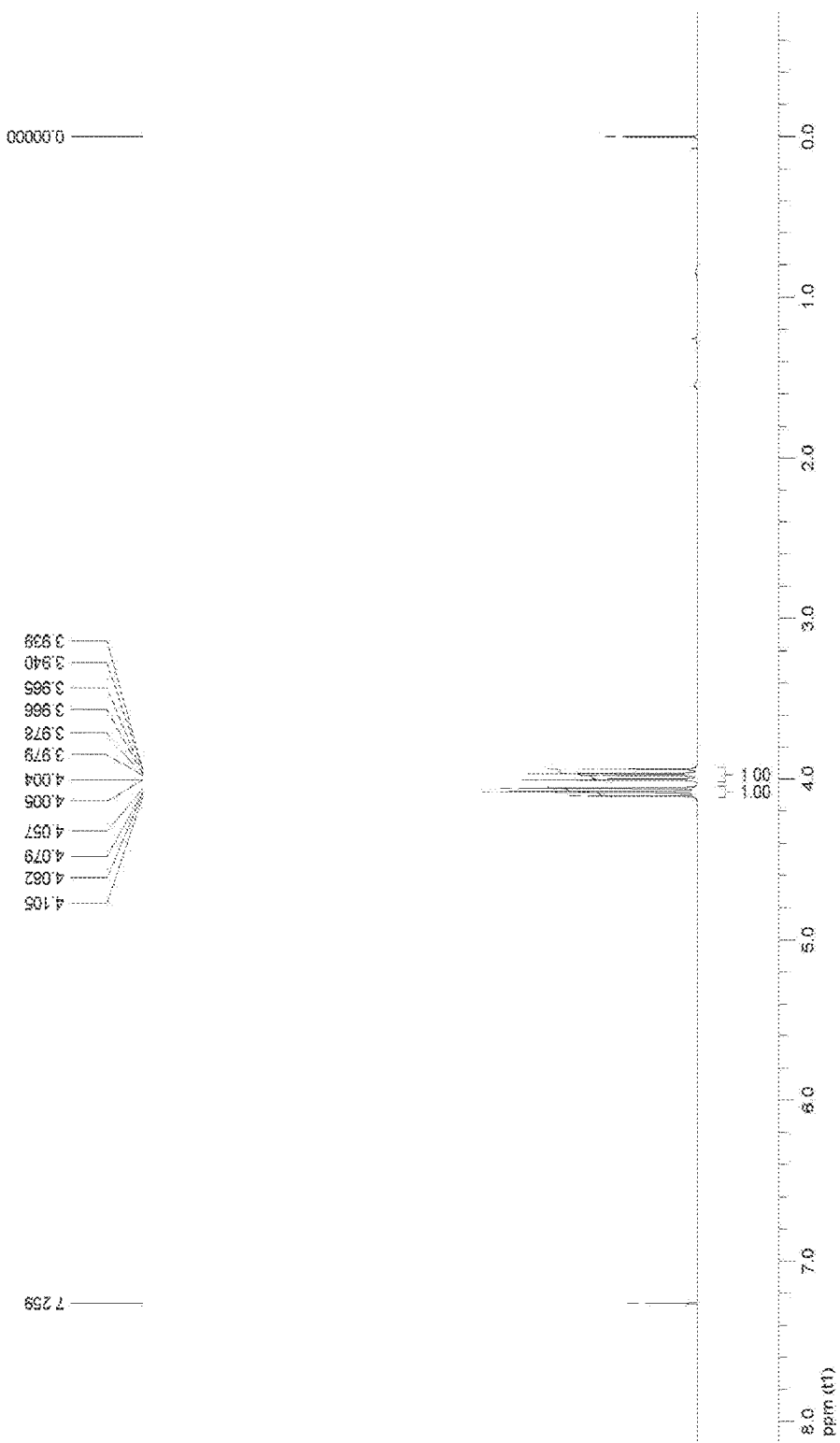

FIG. 3: $^1$H-NMR (500 MHz, CDCl$_3$) δ 4.08 (m, $^3J_{H-F}$= 11.5 Hz, 1H), 3.99 (m, $^4J_{H-F}$=0.5 Hz, $^3J_{H-F}$=13 Hz, 1H).

Figure 4:
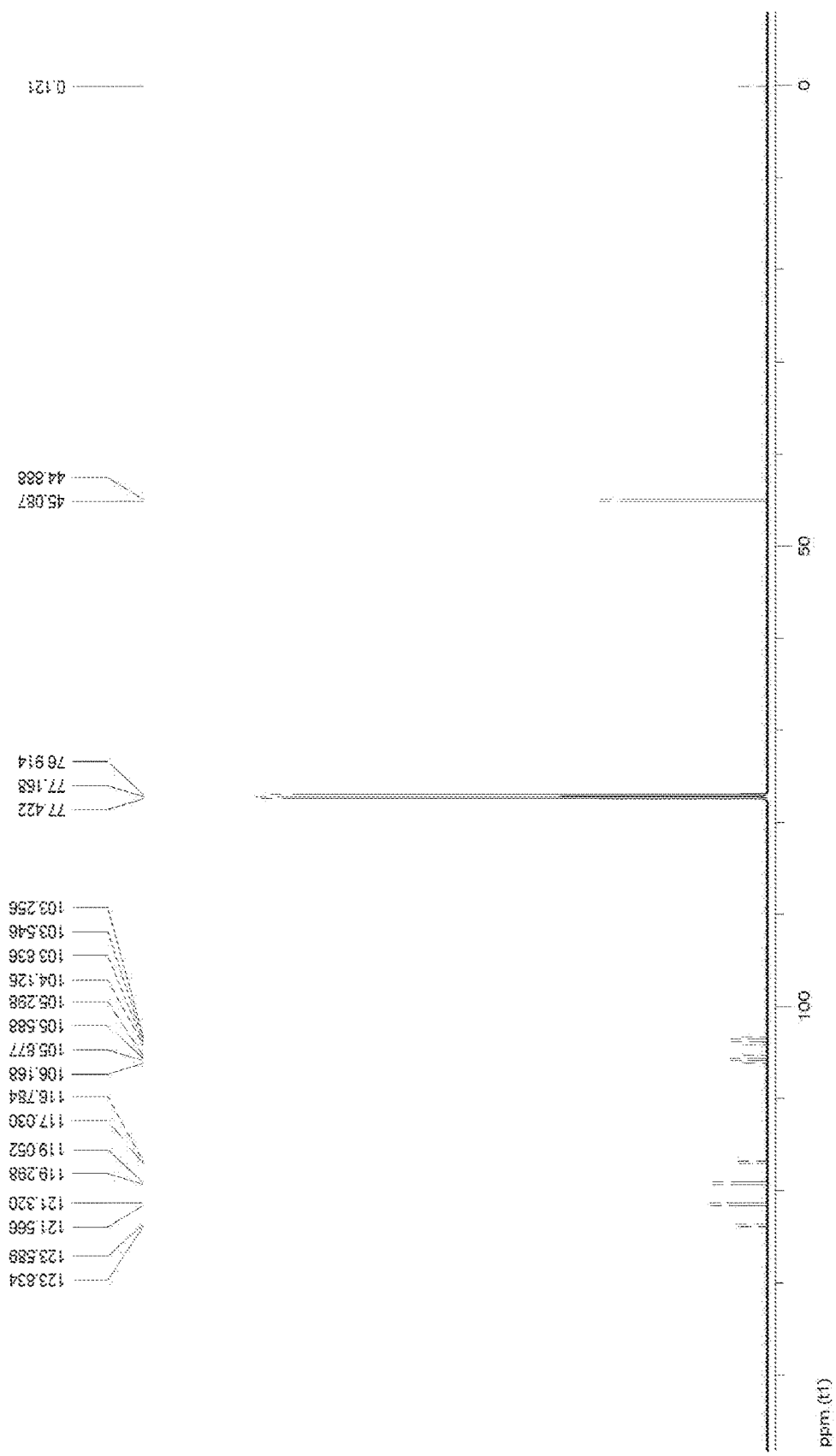

FIG. 4: $^{13}$C-NMR (500 MHz, CDCl$_3$) δ 120.31 (qd, $^1J_{C-F}$=1134.5 Hz, $^2J_{C-F}$=122.5 Hz, 1C), 104.71 (dq, $^1J_{C-F}$= 1021 Hz, $^2J_{C-F}$=145 Hz, 1C), 44.99 (d, $J_{C-F}$=99.5 Hz, 1C).

Figure 5:
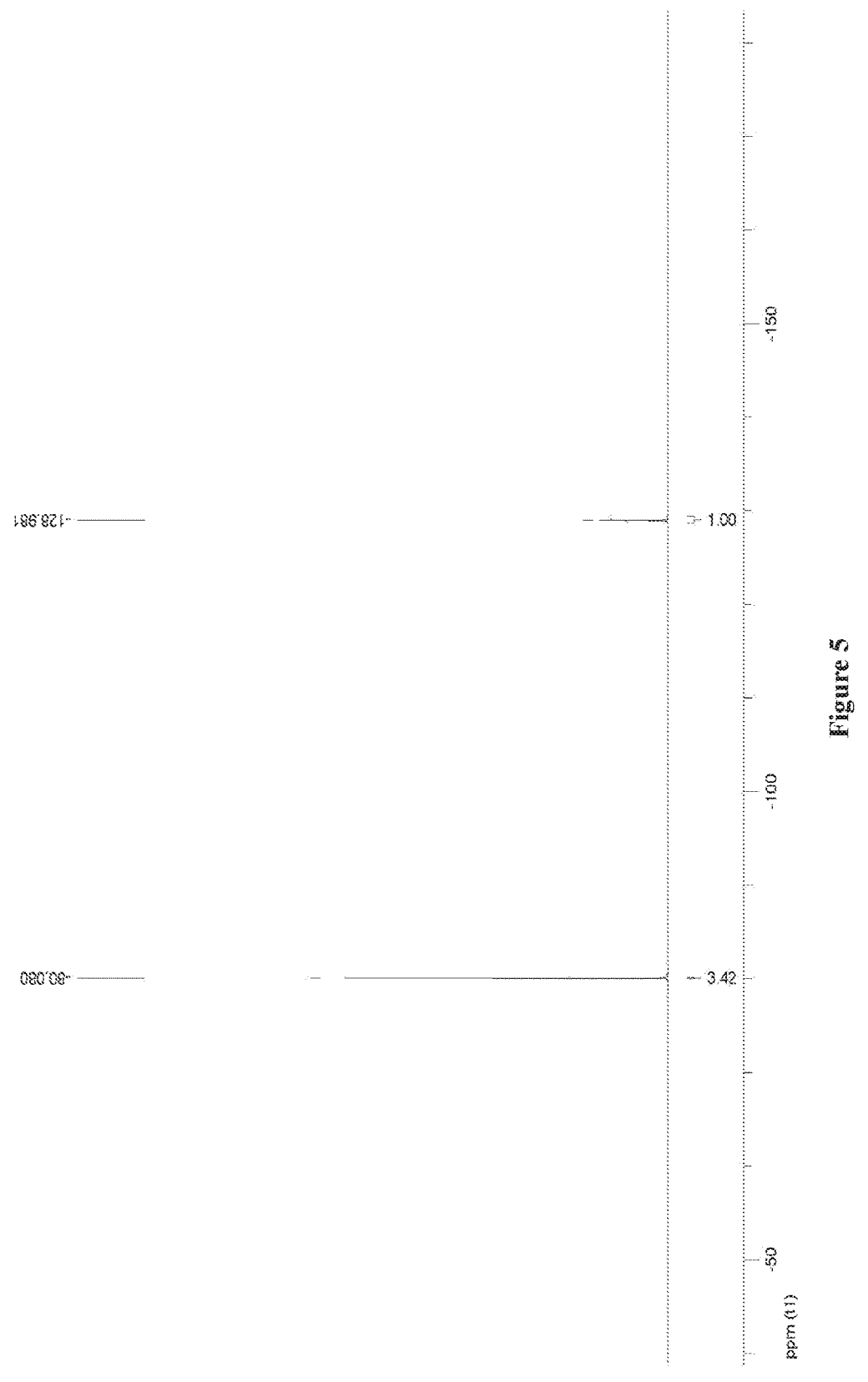

FIG. 5: $^{19}$F-NMR (500 MHz, CDCl$_3$) δ-128.98 (s, 1F), -80.08 (s, 3F).

The above-mentioned liquid reaction product was rectified at atmospheric pressure, and the product having a boiling range of 95° C. to 97° C. was collected with a purity of 98.1%. After characterized by GC-MS, the product was identified as HCFC-233bc, as shown in FIG. 6.

Figure 6:
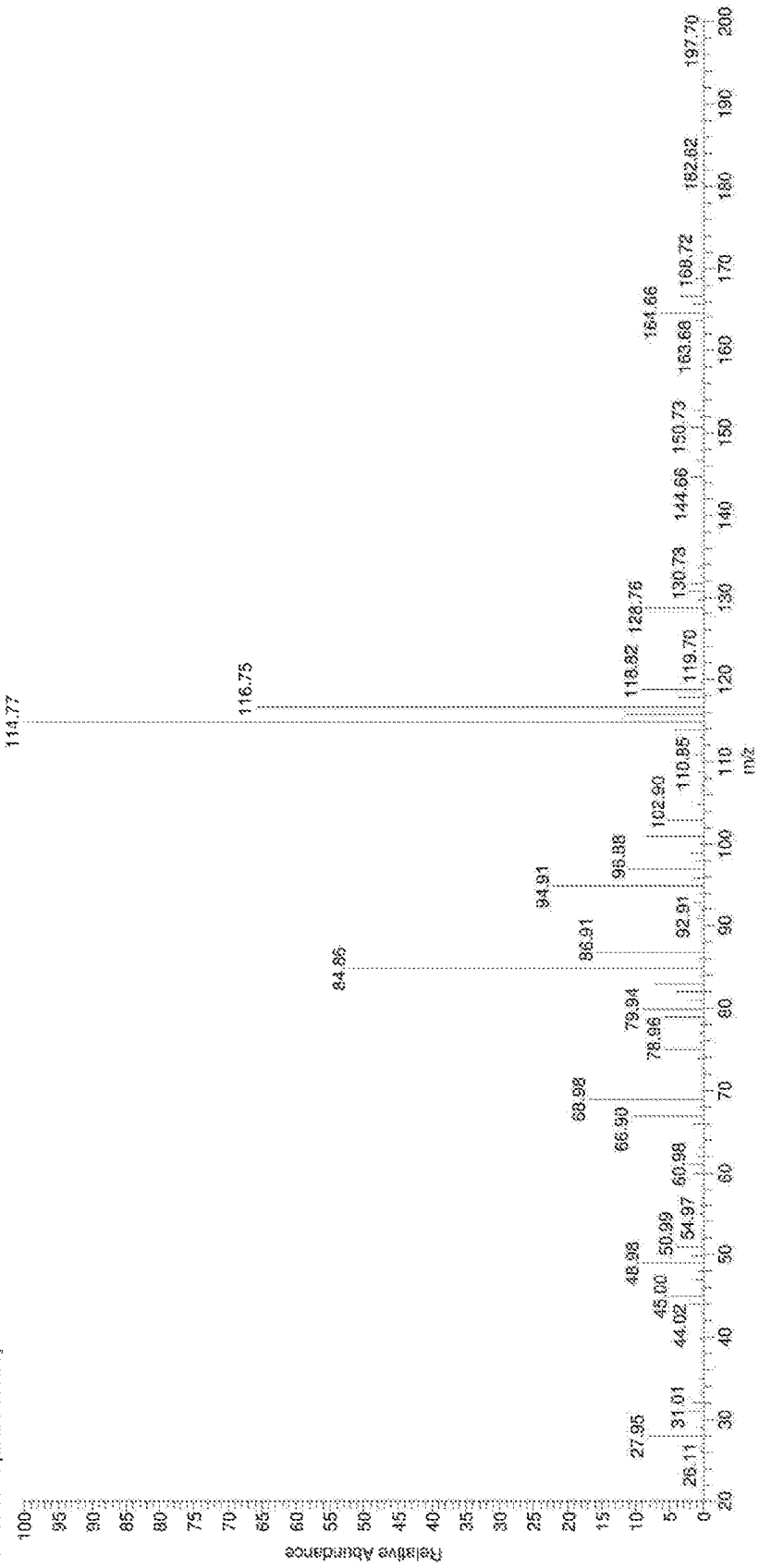
FIG. 6 is a GC-MS spectrum of the product HCFC-233bc.

The mass spectrum results as shown in FIG. 6 and assignment of the peaks therein were as follows: there was no molecular ion peak, m/z165:m/z167:m/z169=9:6:1[(M-Cl)+], which is an isotope peak ratio for the fragment containing two chlorine atoms; m/z129:m/z131=3:1[(M-Cl-HCl)+], which was an isotope peak ratio for the fragment containing one chlorine atom; m/z115:m/z117:m/z119=9:6:1 (CH2FCl2+], which was an isotopic peak ratio for the fragment containing two chlorine atoms, the fragment being a complementary ion to m/z85:m/z87=3:1 (+CF2Cl); m/z75 (C3HF2+), m/z67:m/z69=3:1 (+CHFCl); m/z49:m/z51=3:1 (+CH2Cl); the loss was reasonable, and the compound was HCFC-233bc.

Examples 2-4

In Examples 2 to 4, the reaction was carried out in the same method as in Example 1, except that in Example 1, the reaction temperatures of R1, R2 and R3 were 160° C., 230° C. and 310° C., respectively, while in Examples 2 to 4, the reaction temperatures of R1, R2 and R3 and the reaction results were shown in Table 1.

TABLE 1

| | Reaction temperatures(° C.) | | | Conversion rates (%) | Selectivity (%) | | | | | |
|---|---|---|---|---|---|---|---|---|---|---|
| | | | | | R1 | R2 | | R3 | | |
| Examples | R1 | R2 | R3 | | 231ab | 232ac | 233bc | 234bb | 233bc | 234cc |
| 1 | 160 | 230 | 310 | 100% | 98.3 | 20.3 | 74.9 | 78.7 | 10.5 | 1.5 |
| 2 | 150 | 210 | 290 | 100% | 99.4 | 26.4 | 70.3 | 80.0 | 16.1 | 0.6 |
| 3 | 170 | 240 | 300 | 100% | 97.1 | 17.1 | 77.1 | 69.9 | 21.1 | 2.6 |
| 4 | 180 | 260 | 330 | 100% | 95.8 | 12.8 | 76.4 | 68.3 | 18.4 | 5.2 |

Examples 5-8

In Examples 5 to 8, the reaction was carried out in the same method as in Example 1, except that, in Example 1, the ratio (molar ratio) of HF to organic matters in R1, R2 and R3 were 10:1, 15:1 and 10:1, respectively, and the contact time in R1, R2 and R3 was 5 s, 15 s and 20 s, respectively, while in Examples 5 to 8, the ratio (molar ratio) of HF to organic matters, the contact time and the reaction results were shown in Table 2, wherein the conversion rate of 230ab was 100% in all examples.

TABLE 2

| | Materials proportion (molar ratio) | | | Contact times (s) | | | Selectivity (%) | | | | | |
|---|---|---|---|---|---|---|---|---|---|---|---|---|
| | | | | | | | R1 | R2 | | R3 | | |
| Examples | R1 | R2 | R3 | R1 | R2 | R3 | 231ab | 232ac | 233bc | 234bb | 233bc | 234cc |
| 5 | 5:1 | 10:1 | 5:1 | 5 | 10 | 20 | 99.5 | 26.6 | 68.6 | 77.8 | 12.7 | 1.2 |
| 6 | 10:1 | 15:1 | 15:1 | 10 | 5 | 10 | 98.0 | 47.7 | 49.2 | 70.6 | 27.3 | 0.4 |
| 7 | 15:1 | 10:1 | 10:1 | 20 | 20 | 10 | 97.3 | 11.1 | 84.0 | 60.5 | 36.9 | 0.9 |
| 8 | 20:1 | 15:1 | 20:1 | 30 | 10 | 30 | 97.1 | 29.7 | 67.2 | 59.8 | 20.5 | 5.7 |

Examples 9-12

In Examples 9 to 12, the reaction was carried out in the same method as in Example 1, except that, in Example 1, the molar ratio of Mn, Ni, Zr and Ca in the catalyst was 0.6:3:0.4:6, while in Examples 9-12, the molar ratio was 0.3:4:0.7:5, 0.6:1:0.4:8, 1:2:1:6 and 2:5:0.5:2.5, respectively. The reaction results were shown in Table 3.

TABLE 3

| Ex-am-ples | Molar ratios of Mn, Ni, Zr and Ca | Con-version rates (%) | Selectivity (%) | | | | | |
|---|---|---|---|---|---|---|---|---|
| | | | R1 | R2 | | R3 | | |
| | | | 231ab | 232ac | 233bc | 234bb | 233bc | 234cc |
| 9  | 0.3:4:0.7:5    | 100% | 97.0 | 14.4 | 78.4 | 73.1 | 14.4 | 1.4 |
| 10 | 0.6:1:0.4:8    | 100% | 99.6 | 31.2 | 66.7 | 68.4 | 28.5 | 0.4 |
| 11 | 1:2:1:6        | 100% | 98.1 | 18.9 | 75.6 | 80.3 | 15.4 | 0.8 |
| 12 | 2:5:0.5:2.5    | 100% | 96.3 | 7.9  | 80.2 | 54.1 | 16.2 | 6.9 |

Examples 13 to 19

In Examples 13 to 19, the reaction was carried out in the same method as in Example 1, except that the catalyst in Example 1 was a Mn—Ni—Zr—Ca compound catalyst, while the catalysts in Examples 13 to 19 were Mn—Ni—La—Ca, Mn—Fe—Zr—Mg, Mn—Fe—La—Mg, Mn—Co—Y—Ca, Mn—Co—Y—Ba, Mn—Ni—Y—Ca and Mn—Fe—Y—Ca respectively. The results were shown in Table 4.

TABLE 4

| Examples | Catalysts | Conversion rates (%) | Selectivity (%) | | | | | |
|---|---|---|---|---|---|---|---|---|
| | | | R1 | R2 | | R3 | | |
| | | | 231ab | 232ac | 233bc | 234bb | 233bc | 234cc |
| 13 | Mn—Ni—La—Ca | 100% | 98.2 | 22.6 | 72.7 | 78.5 | 12.2 | 1.3 |
| 14 | Mn—Fe—Zr—Mg | 100% | 94.5 | 10.7 | 79.4 | 57.1 | 13.2 | 7.5 |
| 15 | Mn—Fe—La—Mg | 100% | 92.1 | 8.3  | 82.5 | 65.1 | 17.4 | 5.0 |
| 16 | Mn—Co—Y—Ca  | 100% | 97.4 | 21.2 | 74.9 | 73.6 | 16.5 | 1.9 |
| 17 | Mn—Co—Y—Ba  | 100% | 98.0 | 20.4 | 76.7 | 67.8 | 26.6 | 0.7 |
| 18 | Mn—Ni—Y—Ca  | 100% | 99.1 | 32.9 | 64.7 | 66.2 | 30.4 | 0.5 |
| 19 | Mn—Fe—Y—Ca  | 100% | 97.5 | 25.3 | 70.1 | 74.8 | 13.5 | 1.8 |

Example 20

Preparation of the catalyst: $V_2O_5$ was added to a mixed aqueous solution of $Mg(NO_3)_2 \cdot 6H_2O$ and $Cu(NO_3)_2 \cdot 3H_2O$ according to a certain proportion, 10% (by mass) ammonium bicarbonate was added, the pH was adjusted to about 9, and the reaction was carried out for about 5 h. The product was washed, centrifugally separated, dried at 120° C., and then calcined as follows: calcining at 200° C. for 1 h, heating at a rate of 5° C./min to 300° C., calcining for 2 h, then heating at a rate of 5° C./min to 450° C. and calcining for 4 h. Finally, the product was activated with hydrogen fluoride and hydrogen successively to obtain the catalyst.

To a fixed-bed tubular reactor having an inner diameter of 38 mm, 50 ml of the Cu—V—Mg—F catalyst in which the molar ratio of Cu, V and Mg is 4:1:5 was charged, and then $H_2$ was introduced at 280° C. Two hours later, the materials which came from the bottom of the phase separator and had been subjected to acid-removal and drying, i.e. 2,3-dichloro-1,1,1,2-tetrafluoropropane, 1,2,3-trichloro-1,1,2-trifluoropropane and 1,3-dichloro-1,1,2,2-tetrafluoropropane (the percentages by weight thereof were 88.6%, 6.1% and 4.5%, respectively), were introduced to carry out reaction at an atmospheric pressure (ordinary pressure), wherein the molar ratio of hydrogen to the total amount of 2,3-dichloro-1,1,1,2-tetrafluoropropane, 1,2,3-trichloro-1,1,2-trifluoropropane and 1,3-dichloro-1,1,2,2-tetrafluoropropane was controlled at 0.3:1, the contact time was 30 seconds, and the reaction results were analyzed by gas chromatography and mass spectrometry. While HFO-1234yf and HCFO-1233yf were generated, the by-products $CF_3CF=CClH$ (HCFO-1224yd) and $CF_3CFHCH_3$ (HCFC-254eb) appeared. The reaction results were shown in Table 5, wherein, the conversion rate of the dehalogenation reaction was a sum of the conversion rates of HCFC-234bb, HCFC-233bc and HCFC-234cc.

Figure 7:
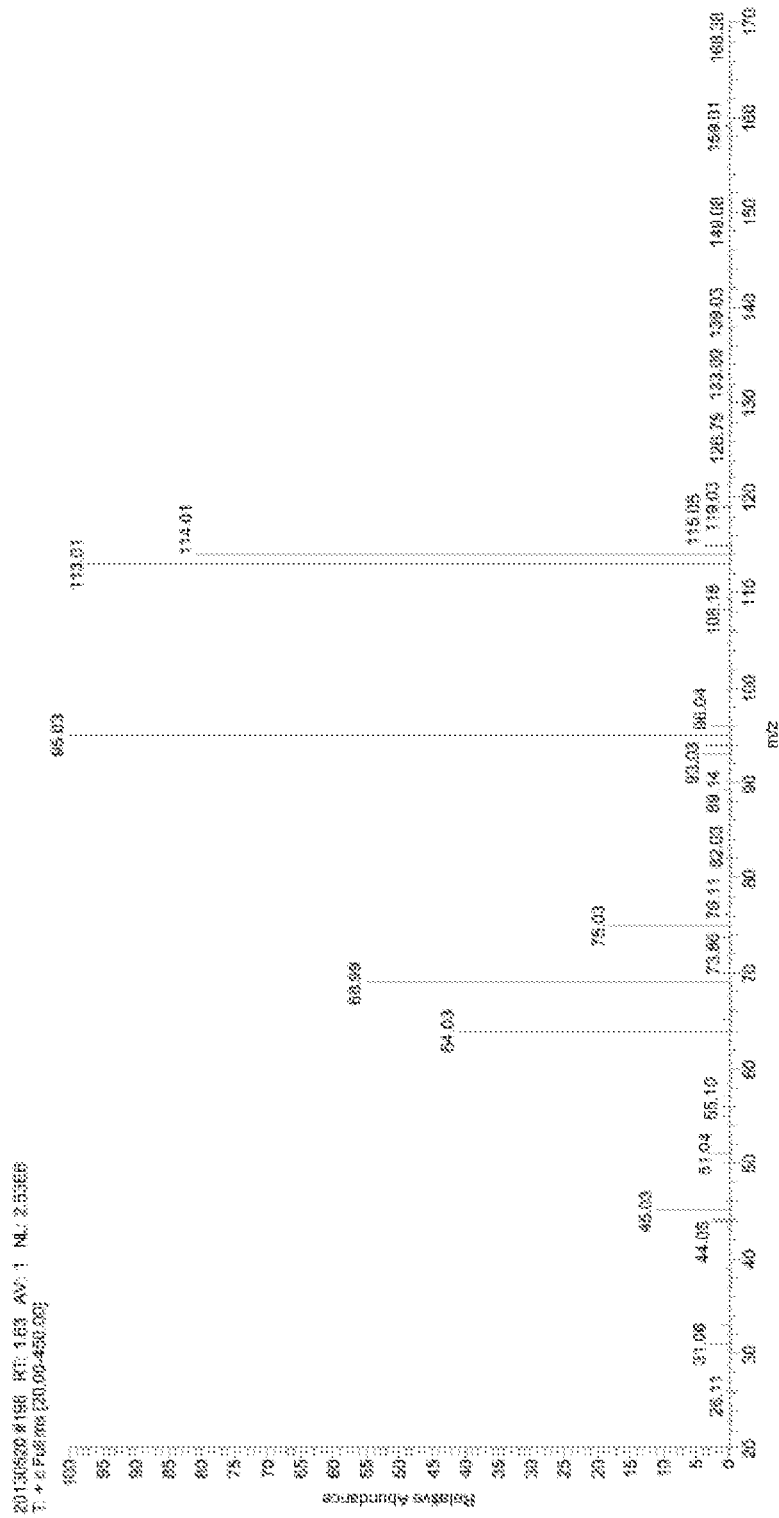
FIG. 7 is a GC-MS spectrum of the product HFO-1234yf.

The target product HFO-1234yf was characterized and identified by GC-MS, as shown in FIG. 7.

Boiling point: −28° C.

The mass spectrum as shown in FIG. 7 and assignment of the peaks therein were as follows: m/z114 (M+); m/z95 [(M−F)+]; m/z75 (C3HF2+); m/z69 (CF3+); m/z64 (C2H2F2+); m/z45 (C2H2F+); m/z44 (C2HF+); the loss was reasonable, and the compound was 2,3,3,3-tetrafluoropropene.

Figure 8:
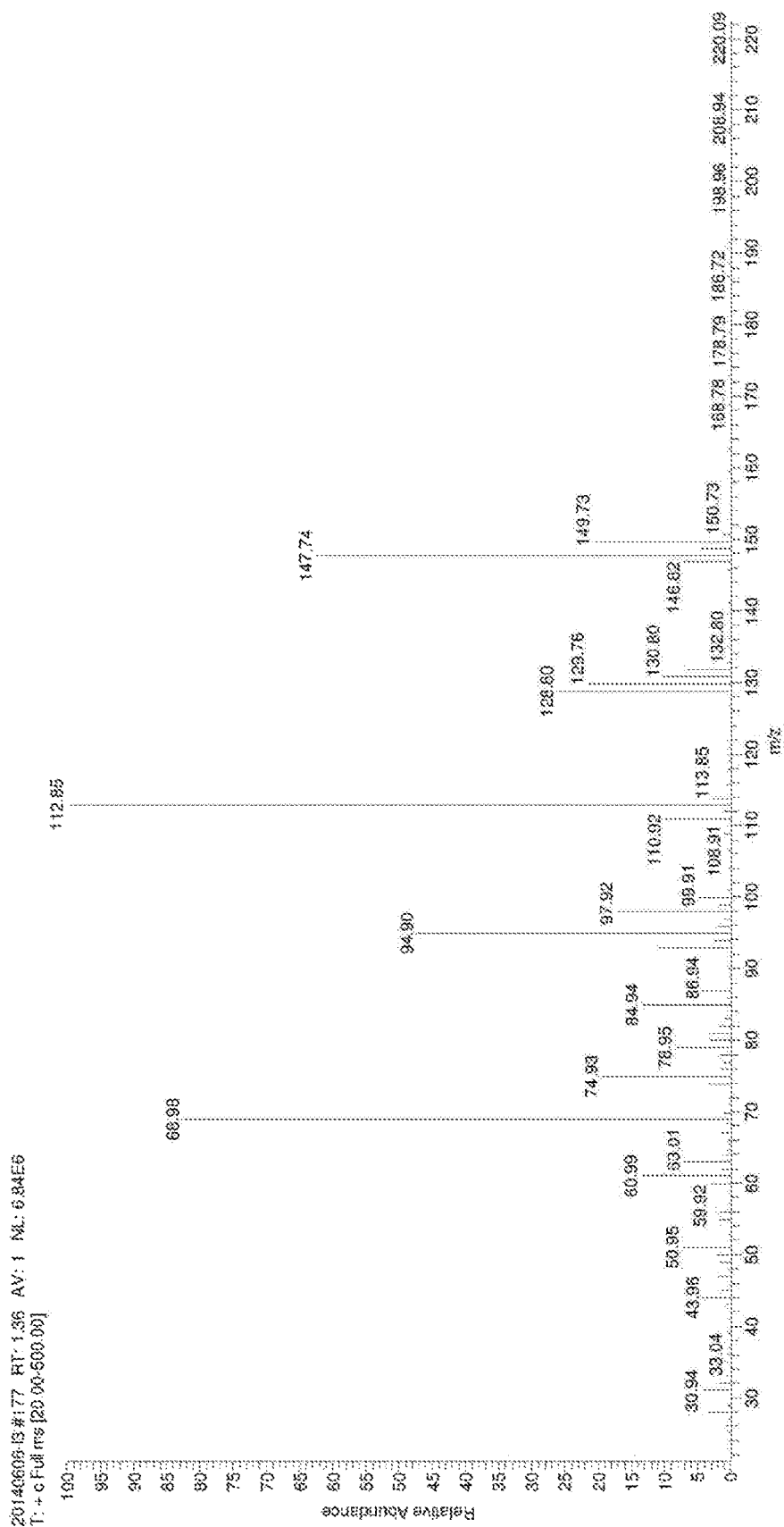
FIG. 8 is a GC-MS spectrum of the product HCFO-1224yd.

The by-product HCFO-1224yd was characterized and identified by GC-MS, as shown in FIG. 8.

Boiling point: 14° C. to 16° C.

The mass spectrum as shown in FIG. 8 and assignment of the peaks therein were as follows: m/z148:m/z150=3:1 (M+), which was the isotopic ratio for the fragment containing one chlorine atom; m/z113[(M−Cl)+], m/z129:m/z131=3:1 [(M−F)+], which was the isotopic ratio for the fragment containing one chlorine atom, the loss was reasonable; m/z69 (CF3+) and m/z79 (C2HFCl+) were complementary ions; m/z75 (C3HF2+); m/z51 (CHF2+); the compound was 1-chloro-2,3,3,3-tetrafluoropropene.

Examples 21 to 24

In Examples 21 to 24, 2,3,3,3-tetrafluoropropene was prepared in the same method as described in Example 20, except that the reaction temperature in Example 20 was 280° C., while in Examples 21 to 24, the reaction temperatures were 200° C., 240° C., 260° C. and 300° C., respectively. The reaction results were shown in Table 5.

TABLE 5

| Examples | Reaction temperatures | Conversion rates of dehalogenation reaction (%) | Product distribution (%) | |
|---|---|---|---|---|
| | | | HFO-1234yf | HCFO-1233yf |
| 20 | 280 | 81.3 | 92.4 | 2.9 |
| 21 | 200 | 50.8 | 93.3 | 5.1 |

TABLE 5-continued

| Examples | Reaction temperatures | Conversion rates of dehalogenation reaction (%) | Product distribution (%) | |
|---|---|---|---|---|
| | | | HFO-1234yf | HCFO-1233yf |
| 22 | 240 | 74.6 | 92.9 | 4.7 |
| 23 | 260 | 90.6 | 90.5 | 1.6 |
| 24 | 300 | 100 | 86.7 | 0.8 |

Examples 25 to 28

In Examples 25 to 28, 2,3,3,3-tetrafluoropropene was prepared in the same method as described in Example 20, except that the molar ratio of Cu, V and Mg in the catalyst of Example 20 was 4:1:5, while the molar ratios in the catalysts of Examples 25 to 28 were 2:1:7, 3:1:6, 3:2:5 and 4:2:4, respectively. The reaction results were shown in Table 6.

TABLE 6

| Examples | Molar ratios of Cu, V and Mg | Conversion rates of dehalogenation reaction (%) | Product distribution (%) | |
|---|---|---|---|---|
| | | | HFO-1234yf | HCFO-1233yf |
| 25 | 2:1:7 | 74.3 | 92.5 | 3.8 |
| 26 | 3:1:6 | 87.9 | 92.8 | 4.3 |
| 27 | 3:2:5 | 100 | 64.7 | 0.2 |
| 28 | 4:2:4 | 62.4 | 93.1 | 4.9 |

Examples 29 to 31

In Examples 29 to 31, 2,3,3,3-tetrafluoropropene was carried out in the same method as described in Example 20, except that the molar ratio of hydrogen to the total amount of HCFC-233bc, HCFC-234bb and HCFC-234cc was 0.3:1 in Example 20, while in Examples 29 to 31, the molar ratios were 0.1:1, 0.5:1 and 1:1, respectively. The reaction results were shown in Table 7.

TABLE 7

| Examples | Molar ratios | Conversion rates of dehalogenation reaction (%) | Product distribution (%) | |
|---|---|---|---|---|
| | | | HFO-1234yf | HCFO-1233yf |
| 29 | 0.1:1 | 72.5 | 92.3 | 4.1 |
| 30 | 0.5:1 | 85.3 | 90.1 | 1.2 |
| 31 | 1:1 | 91.7 | 86.7 | 0.9 |

Examples 32 to 35

In Examples 32 to 35, 2,3,3,3-tetrafluoropropene was prepared in the same method as described in Example 20, except that the contact time in Example 20 was 30 s, while in Examples 32 to 35, the contact times were 5 s, 10 s, 20 s and 50 s, respectively. The reaction results were shown in Table 8.

TABLE 8

| Examples | Contact times (s) | Conversion rates of dehalogenation reaction (%) | Product distribution (%) | |
|---|---|---|---|---|
| | | | HFO-1234yf | HCFO-1233yf |
| 32 | 5 | 58.6 | 93.5 | 4.8 |
| 33 | 10 | 70.9 | 92.8 | 4.5 |
| 34 | 20 | 76.6 | 92.6 | 3.6 |
| 35 | 50 | 93.4 | 91.4 | 2.7 |

Example 36

In Example 36, 2,3,3,3-tetrafluoropropene was prepared in the same method as described in Example 20, except that the reaction material in Example 20 was a mixture of 2,3-dichloro-1,1,1,2-tetrafluoropropane, 1,2,3-trichloro-1,1,2-trifluoropropane and 1,3-dichloro-1,1,2,2-tetrafluoropropane (percentages by mass thereof were 88.6%, 6.1% and 4.5%), while in Example 36, the reaction material was HCFC-234bb. The reaction results showed that the reaction conversion was 93.4%, and the selectivity of HFO-1234yf was 99.0%.

Example 37

In Example 37, 2,3,3,3-tetrafluoropropene was prepared in the same method as described in Example 20, except that, the reaction material in Example 20 was a mixture of 2,3-dichloro-1,1,1,2-tetrafluoropropane, 1,2,3-trichloro-1,1,2-trifluoropropane and 1,3-dichloro-1,1,2,2-tetrafluoropropane (percentages by mass thereof were 88.6%, 6.1% and 4.5%), while in Example 37, the reaction material was HCFC-233bc. The reaction results showed that the reaction conversion was 100%, and the selectivity was 95.9%.

Example 38

In Example 38, 2,3,3,3-tetrafluoropropene was prepared in the same method as described in Example 20, except that the reaction material in Example 20 was a mixture of 2,3-dichloro-1,1,1,2-tetrafluoropropane, 1,2,3-trichloro-1,1,2-trifluoropropane and 1,3-dichloro-1,1,2,2-tetrafluoropropane (percentages by mass thereof were 88.6%, 6.1% and 4.5%), while in Example 38, the reaction material was HCFC-234cc. The reaction results showed that the reaction conversion was 97.5%, and the selectivity was 93.8%.

The foregoing is only a part of examples of the present invention and not intended to limit the scope of the invention. Any simple changes, equivalent variations and modifications to the above-mentioned examples in accordance with the technical essence of the present invention fall within the scope of the technical solutions of the present invention.

What is claimed is:

1. A process for the preparation of 2,3,3,3-tetrafluoropropene, comprising the following steps:
    (a) a compound having the formula $CF_{3-x}Cl_xCF_{2-y}Cl_yCH_2Cl$ undergoes gas-phase fluorination with hydrogen fluoride in the presence of a compound catalyst through n serially-connected reactors to produce a product stream comprising 2,3-dichloro-1,1,1,2-tetrafluoropropane, 1,2,3-trichloro-1,1,2-trifluoropropane, 1,3-dichloro-1,1,2,2-tetrafluoropropane, hydrogen chloride and unreacted hydrogen fluoride; wherein in the compound formula, x=1, 2 or 3, y=1 or 2, and $3 \le x+y \le 5$;

(b) 2,3-dichloro-1,1,1,2-tetrafluoropropane, 1,2,3-trichloro-1,1,2-trifluoropropane, and 1,3-dichloro-1,1,2,2-tetrafluoropropane undergo gas-phase dehalogenation with hydrogen in the presence of a dehalogenation catalyst to produce a product stream comprising 2,3,3,3-tetrafluoropropene, 3-chloro-2,3,3-trifluoropropene, hydrogen chloride and unreacted hydrogen;

(c) the product stream of step (a) enters into the first rectification column for hydrogen chloride separation, and the component from the top of the column which is hydrogen chloride, enters into an acid production system to obtain hydrochloric acid; the components from the bottom of the column which are 2,3-dichloro-1,1,1,2-tetrafluoropropane, 1,2,3-trichloro-1,1,2-trifluoropropane, 1,3-dichloro-1,1,2,2-tetrafluoropropane and hydrogen fluoride, enter into a phase separator for phase separation; the phase separation temperature is −30° C. to 0° C., the phase separator bottom materials 2,3-dichloro-1,1,1,2-tetrafluoropropane, 1,2,3-trichloro-1,1,2-trifluoropropane and 1,3-dichloro-1,1,2,2-tetrafluoropropane are subjected to acid-removal and drying, and then are transported as raw materials of step (b) to a dehalogenation reactor for dehalogenation reaction; and (d) the product stream of step (b) enters into the second rectification column, the component from the bottom of the column which is 3-chloro-2,3,3-trifluoropropene, is subjected to acid-removal and drying, and then is recycled to the serially-connected reactors of step (a); the components from the top of the column which are 2,3,3,3-tetrafluoropropene, hydrogen chloride and hydrogen enter into the third rectification column; in the third rectification column, the components from the top of the column which are hydrogen and hydrogen chloride, enter into the hydrogen recovery system, the hydrogen is recycled to a dehalogenation reactor for dehalogenation reaction, and the components from the bottom of the column which are 2,3,3,3-tetrafluoropropene and hydrogen chloride, are subjected to refining and drying to produce the target product 2,3,3,3-tetrafluoropropene.

2. The process for the preparation of 2,3,3,3-tetrafluoropropene according to claim 1, characterized in that the compound having the formula $CF_{3-x}Cl_xCF_{2-y}Cl_yCH_2Cl$ in step (a) is $CCl_3CCl_2CH_2Cl$, $CFCl_2CCl_2CH_2Cl$ or $CF_2ClCCl_2CH_2Cl$.

3. The process for the preparation of 2,3,3,3-tetrafluoropropene according to claim 2, characterized in that the compound having the formula $CF_{3-x}Cl_xCF_{2-y}Cl_yCH_2Cl$ in step (a) is $CCl_3CCl_2CH_2Cl$.

4. The process for the preparation of 2,3,3,3-tetrafluoropropene according to claim 1, characterized in that the compound catalyst in step (a) is a Mn-A-B-C compound catalyst, wherein A is a Group VIII element, B is a high-field-strength element, and C is an alkaline-earth metal element; the molar ratio of Mn, A, B and C is (0.3-2):(0.6-5):(0.1-1):(2-9); the process for the preparation of catalyst comprises the following steps: a mixed solution of soluble salts of the three metals Mn, A and B is reacted with a precipitant in proportion, the pH is controlled at 7.5 to 9.5, stirring, precipitating, filtering and drying are conducted, then an oxide, hydroxide or carbonate of C is well mixed therewith, then staged calcination is performed at 200° C. to 500° C. under a condition of no less than three temperature gradients, and finally activation treatment is carried out with hydrogen fluoride at 200° C. to 380° C. to obtain the catalyst.

5. The process for the preparation of 2,3,3,3-tetrafluoropropene according to claim 4, characterized in that, in the Mn-A-B-C compound catalyst in step (a), A is one of Ni, Fe and Co or a combination of two or more thereof, B is one of Zr, Y and La or a combination of two or more thereof, and C is one of Mg, Ca and Ba; and the molar ratio of Mn, A, B and C is (0.6-1):(2-4):(0.4-1):(4-7).

6. The process for the preparation of 2,3,3,3-tetrafluoropropene according to claim 5, characterized in that the Mn-A-B-C compound catalyst in step (a) is Mn—Ni—Zr—Ca compound catalyst, wherein the molar ratio of Mn, Ni, Zr and Ca is 0.6:3:0.4:6.

7. The process for the preparation of 2,3,3,3-tetrafluoropropene according to claim 1, characterized in that the n serially-connected reactors in step (a) are three serially-connected reactors arranged in series in the flowing direction of the raw material and charged with the compound catalyst, which have sequentially increased reaction temperatures.

8. The process for the preparation of 2,3,3,3-tetrafluoropropene according to claim 7, characterized in that the increasing range of the reaction temperature between the three serially-connected reactors is 60° C. to 80° C.

9. The process for the preparation of 2,3,3,3-tetrafluoropropene according to claim 7, characterized in that at least a separation tank is installed between the primary and secondary reactors in the three serially-connected reactors, the components from the top of the separation tank which are 2,3,3,3-tetrafluoropropene and hydrogen chloride, enter into a second rectification column; and the components from the bottom of the separation tank are 1,1,2,2,3-pentachloro-1-fluoropropane and/or 1,2,2,3-tetrachloro-1,1-difluoropropane or 1,1,1,2,2,3-hexachloropropane and hydrogen fluoride.

10. The process for the preparation of 2,3,3,3-tetrafluoropropene according to claim 7, characterized in that, the conditions for the gas-phase fluorination reaction in the primary reactor of the three serially-connected reactors are as follows: the reaction temperature is 150° C. to 180° C., the molar ratio of hydrogen fluoride to $CCl_3CCl_2CH_2Cl$ is 3-20:1, and the reaction contact time is 0.5 to 30 seconds.

11. The process for the preparation of 2,3,3,3-tetrafluoropropene according to claim 1, characterized in that the dehalogenation catalyst in step (b) is a Cu—V—Mg—F catalyst in which the molar ratio of Cu, V and Mg is (2-4):(1-2):(4-7); the conditions for the gas-phase dehalogenation are as follows: the reaction temperature is 200° C. to 300° C., the molar ratio of hydrogen to the total amount of 2,3-dichloro-1,1,1,2-tetrafluoropropane, 1,2,3-trichloro-1,1,2-trifluoropropane, and 1,3-dichloro-1,1,2,2-tetrafluoropropane is (0-1):1, and the contact time is 1 to 30 seconds.

12. The process for the preparation of 2,3,3,3-tetrafluoropropene according to claim 1, characterized in that the component from the bottom of the column 3-chloro-2,3,3-trifluoropropene of the second rectification column from step (d) is recycled to the primary reactor of the serially-connected reactors in step (a).

* * * * *